(12) United States Patent
Mercer et al.

(10) Patent No.: US 9,463,285 B2
(45) Date of Patent: Oct. 11, 2016

(54) MEDICATED MODULE WITH LOCK FEATURE

(75) Inventors: David Richard Mercer, Warwickshire (GB); Garen Kouyoumjian, Warwickshire (GB); Malcolm Stanley Boyd, Warwickshire (GB); Michael Bainton, Warwickshire (GB); John David Cross, Northhamptonshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 127 days.

(21) Appl. No.: 14/110,540

(22) PCT Filed: Apr. 19, 2012

(86) PCT No.: PCT/EP2012/057154
§ 371 (c)(1),
(2), (4) Date: Oct. 8, 2013

(87) PCT Pub. No.: WO2012/143437
PCT Pub. Date: Oct. 26, 2012

(65) Prior Publication Data
US 2014/0094757 A1    Apr. 3, 2014

(30) Foreign Application Priority Data

Apr. 21, 2011  (EP) .................................. 11163377

(51) Int. Cl.
*A61M 5/32* (2006.01)
*A61M 5/24* (2006.01)
(Continued)

(52) U.S. Cl.
CPC .......... *A61M 5/3294* (2013.01); *A61M 5/2448* (2013.01); *A61M 5/326* (2013.01);
(Continued)

(58) Field of Classification Search
CPC ................ A61M 2005/3267; A61M 5/326;
A61M 5/3294; A61M 5/2448; A61M 5/347; A61M 5/2033; A61M 2005/2013; A61M 5/2066; A61M 5/24; A61M 5/28
USPC ........................ 604/82, 191, 192, 198, 205
See application file for complete search history.

(56) References Cited

U.S. PATENT DOCUMENTS 5,695,475 A * 12/1997 Best et al. .................... 604/198
6,562,002 B1 * 5/2003 Taylor ............................. 604/82
(Continued)

FOREIGN PATENT DOCUMENTS

FR          1256429       3/1961
JP       2003-534105 A   11/2003
(Continued)

OTHER PUBLICATIONS

International Search Report and Written Opinion for Int. App. No. PCT/EP2012/057154, mailed Jul. 30, 2012.
(Continued)

*Primary Examiner* — Kevin C Sirmons
*Assistant Examiner* — William Carpenter
(74) *Attorney, Agent, or Firm* — McDonnell Boehnen Hulbert & Berghoff LLP

(57) ABSTRACT

A medicated module for an injection system to co-deliver at least two medicaments is disclosed where a primary delivery device containing a primary medicament accepts a medicated module containing a single dose of a secondary medicament and where both medicaments are delivered through a hollow needle. The medicated module is initially in a locked state until attached to a drug delivery where interaction of the cartridge holder with the module bypass housing changes the module to a triggerable state. The medicated module does not require the user to manually engage a reservoir containing the secondary medicament. Instead, a biasing member automatically activates the reservoir when the needle guard is retracted when the module is in the triggerable state. The needle guard prevents accidental needle sticks before and after an injection, and locks after removal from the injection site.

26 Claims, 6 Drawing Sheets

(51) Int. Cl.
   *A61M 5/31*     (2006.01)
   *A61M 5/315*    (2006.01)
   *A61M 5/34*     (2006.01)
   *A61M 5/178*    (2006.01)
   *A61M 5/20*     (2006.01)

(52) U.S. Cl.
   CPC ......... *A61M 5/2466* (2013.01); *A61M 5/3146* (2013.01); *A61M 5/31533* (2013.01); *A61M 5/3245* (2013.01); *A61M 5/347* (2013.01); *A61M 2005/1787* (2013.01); *A61M 2005/2073* (2013.01); *A61M 2005/3247* (2013.01); *A61M 2005/3267* (2013.01); *A61M 2205/581* (2013.01); *A61M 2205/582* (2013.01); *A61M 2205/583* (2013.01); *A61M 2205/588* (2013.01)

(56) References Cited

U.S. PATENT DOCUMENTS

| | | | |
|---|---|---|---|
| 2001/0037087 A1* | 11/2001 | Knauer | 604/137 |
| 2003/0139705 A1 | 7/2003 | Larsen et al. | |
| 2008/0221528 A1* | 9/2008 | Lanz | 604/192 |
| 2012/0136316 A1* | 5/2012 | Davies et al. | 604/191 |
| 2013/0018323 A1* | 1/2013 | Boyd et al. | 604/191 |
| 2013/0204186 A1* | 8/2013 | Moore et al. | 604/111 |
| 2013/0237932 A1* | 9/2013 | Thueer et al. | 604/272 |
| 2013/0245562 A1* | 9/2013 | Kouyoumjian et al. | 604/191 |
| 2013/0245563 A1* | 9/2013 | Mercer et al. | 604/191 |
| 2014/0025015 A1* | 1/2014 | Cross et al. | 604/198 |

FOREIGN PATENT DOCUMENTS

| | | |
|---|---|---|
| WO | 01/91837 A1 | 12/2001 |
| WO | 2009/022132 | 2/2009 |
| WO | 2010/126432 A1 | 11/2010 |
| WO | 2010/139671 | 12/2010 |
| WO | 2010/139672 | 12/2010 |
| WO | 2010/147552 A1 | 12/2010 |
| WO | WO 2011117287 A1 * | 9/2011 |

OTHER PUBLICATIONS

International Preliminary Report on Patentability for Int. App. No. PCT/EP2012/057154, mailed Oct. 31, 2013.

Japanese Office Action for JP App. No. 2014-505621, dated Mar. 8, 2016.

* cited by examiner

FIG. 11A  FIG. 11B

MEDICATED MODULE WITH LOCK FEATURE

CROSS REFERENCE TO RELATED APPLICATIONS

The present application is a U.S. National Phase Application pursuant to 35 U.S.C. §371 of International Application No. PCT/EP2012/057154 filed Apr. 19, 2012, which claims priority to European Patent Application No. 11163377.2 filed Apr. 21, 2011. The entire disclosure contents of these applications are herewith incorporated by reference into the present application.

FIELD OF THE DISCLOSURE

This invention relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, our invention concerns a medicated module where the user does not have to manually select or set the module to dispense the second drug agent because activation of the needle guard automatically causes the reservoir of secondary medicament to engage with dispensing conduits. Our invention includes a locked configuration to prevent premature activation or triggering of the module prior to use.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. Our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Our invention also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

A number of medical and pharmaceutical drug delivery devices known in the art utilize the release of stored energy to drive some part of their mechanism during use. This energy may be stored in various forms including elastic (e.g. a spring), electrical, chemical, potential, pneumatic or hydraulic. In situations where this energy is captured/stored during the manufacturing or assembly process, rather than being provided by the user/patient as part of the use operation (such as winding a spring or pushing a lever), it is important that the energy is not accidentally released (triggered) until the desired moment, i.e., it is not released during transport or storage or similar such handling.

For some medical devices, accidental triggering prior to use may either compromise the operability of the device, or may even render it unusable. This may be of particular importance for single-use devices. For devices containing medicament, and where accidental triggering has the potential to compromise the integrity of the primary package of medicament, such events are likely to be particularly undesirable as they have the potential to result in a patient being exposed to a potentially non-sterile or even harmful, degraded form of the medicament.

Prior to use, the transit and storage of the medical device may present numerous scenarios in which the stored energy could be unintentionally discharged. Factors that may cause an accidental triggering event may include, but are not limited to; the application of static loads (stacking, crushing), dynamic loads (e.g. impact, vibration), pack and/or device inversion or temperature fluctuation.

Latches, locks and similar systems for preventing non-intentional actuation are known in the art (e.g. in the field of fire-arms, auto injectors, etc.). Generally, such features either need to be designed to be intuitive or, more ideally, the system designed in such a way that the shift in state from "locked out" to "triggerable" happens automatically as part of the standard, correct use procedure. Our invention provides such an automatic shift in state that prevents accidental triggering prior to use. Our invention is applicable to any device where energy may be stored in the device prior to delivery to the user, particularly single-use or medicated devices where accidental triggering may render the device unusable. Examples of such devices are auto-injectors, safety needles, safety syringes, needle-free/jet injectors and pressurized medicament cartridges (such as those used in pMDIs).

These and other advantages will become evident from the following more detailed description of the invention.

SUMMARY

Our invention allows complex combinations of multiple drug compounds within a single drug delivery system. The invention allows the user to set and dispense a multi-drug compound device though one single dose setting mechanism and a single dispense interface. This single dose setter controls the mechanism of the device such that a predefined combination of the individual drug compound is delivered when a single dose of one of the medicaments is set and dispensed through the single dispense interface.

By defining the therapeutic relationship between the individual drug compounds our delivery device would help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect this invention is of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one possible medicated module design, a bypass cavity or housing that surrounds the primary pack of medicament, preferably a single dose, is held in an initial priming mode position by stand-offs on the outer body of the module. Rotation of the bypass housing, as a result of axial movement of the needle guard, eventually brings the stand-offs into line with pockets in the outer body, allowing the cavity to move axially in relation to the outer body and therefore engage the primary pack. The present invention prevents accidental triggering by preventing rotation of the bypass housing relative to the outer body housing, using locking features. The locking features move from an initial "locked" state to a "triggerable" state through attachment and interaction with the cartridge holder on the primary device. In the locked state the bypass housing is prevented from rotating by a lockout flat on the outer wall of the bypass housing. In one embodiment, the lock features interact with a tooth and slot engagement between the bypass housing and the upper hub. In the "triggerable" position the bypass housing has been rotated or pushed distally by attachment of the cartridge holder to the upper hub, thereby allowing rotation and eventual firing of the bypass housing at the appropriate time (as the user starts to retract the needle guard for injection and dispense). Stated in another way, the features that cause the locking of the bypass cavity are located between the needle guard and the bypass cavity. All features at the proximal end of the module (i.e., between the upper hub/outer body and bypass) are configured to move the bypass cavity off of the axial lock feature into a triggerable state. That is, rotate the bypass cavity such that the needle guard rib is no longer axially constrained and therefore can cause the bypass cavity to rotate further thus triggering primary pack engagement.

The mechanism of our invention is automatically activated upon attachment of the medicated module to the primary device, which should typically occur only immediately prior to use. No additional use steps by the user are required to activate the module above what is now considered the current "state of the art" for the use of standard needles with existing injection devices.

In one embodiment of our invention there is provided a medicated module attachable to a drug delivery device that comprises an outer housing having an inner surface, a proximal end and a distal end, where the proximal end has an upper hub holding a first double-ended needle cannula and a connector configured for attachment to a drug delivery device. A bypass housing is located inside the outer housing that is configured to move both rotationally and axially in the proximal direction with respect to the outer housing when the module is triggered during use. The bypass housing has an outer surface and a step down edge at the proximal end that allows the bypass housing to move proximally to engage the reservoir with the two needle cannula. The outer surface of the bypass housing can have a non-linear track configured to engage a radial protrusion on the inside surface of the guard. The upper hub has one or more cutouts for functional access to the proximal end of the bypass housing. In one embodiment, the proximal end has a rotation tab that projects radially from the inner surface of the bypass housing and is configured to engage an axially projecting tab on the distal end of a cartridge holder of a primary drug delivery device. Alternatively the rotation tab can project axially from the proximal end of the bypass housing and the tab on the cartridge holder project radially. In yet another embodiment the proximal end of the bypass housing has an engagement recess configured to engage a corresponding tab projecting proximally from the upper hub to prevent rotation and axial movement in the proximal direction when the module is in the locked state.

There is a reservoir within the bypass housing, preferably comprising a single dose of a medicament. The medicated module assembly of our invention contains a needle guard that can reduce the risk of accidental needle sticks before and after use, reduce the anxiety of users suffering from needle phobia as well as preventing a user from using the device a subsequent time when the additional medicament has already been expelled. There is a also a biasing member engaged between the guard and a lower hub located at the distal end of the bypass housing.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be from about 3 to about 4 mm. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the needle guard or shield is configured to move axially in both the distal and proximal directions when pressed against and removed from an injection site. When the needle assembly is removed or withdrawn from the patient, the guard is returned to post-use extended position. A locking mechanism can be used to securely lock the guard from further substantial axial movement at the completion of the injection. A locking mechanism could also be used to further lock the medicated module from any further use and prevent the needle(s) from being reused. Likewise, there can be an additional locking mechanism that prevents the reservoir or needles from being able to substantially move within the system even if the guard is held in an axially locked condition. By "substantial" movement we do not mean the typical amount of "play" in a system, but instead we mean that the guard and/or distal needle do not move axially a distance that exposes the distal end of the cannula once it is locked out.

Manually operated devices are sometimes not as intuitive as they could be and raise the risk of accidental misuse. Our invention solves this problem by utilizing a rotating cylinder that is moved by the retraction of needle guard thus activating the state change from prime dose to combination dose. The mechanism aims to make this actuation imperceptible to the user, consequently making the user experience of the module very similar to that of a standard commercially available and accepted needle or safety needle (i.e. unpack module, attach to a drug delivery device, prime drug delivery device, inject a set dose along with single dose in the module). In this way, the module mechanism aims to reduce the risk of unintentional misuse and to improve usability by replicating an already accepted practice for similar injection methods. However, such automatically triggering devices risk being triggered prematurely.

Another goal of our invention is to prevent premature triggering of the medicated module prior to use. Because the medicated module is designed to eliminate the need to have the user manually operate the medicated module to change the state of the module from a locked/priming state to a combination dose delivery state there is a risk that the automatic triggering system might be accidentally triggered during shipment, storage, or mishandling of the device. To avoid this problem, the proximal end of the bypass housing can be configured to interact with the distal end of a cartridge holder on a drug delivery device such that the bypass housing is rotated or moved distally to change the medicated module from a locked state to a triggering state. In the locked state, rotation of the bypass housing is prevented and thus the engagement of the needle cannulae with the reservoir is prevented.

When the primary drug delivery device is attached to the upper hub of the module, lugs or tabs extending radially or axially on the cartridge holder connection means protrude through the cutouts in the upper hub and engage the rotation tabs on the proximal end of the bypass housing. As the cartridge holder connection means is pushed distally and rotated into the upper hub, the cartridge holder tabs engage the rotation tabs rotating the bypass housing relative to the upper hub until the nonlinear track is rotated so that the needle guard protrusion is aligned with the helical portion of the track. In an alternative embodiment, the cartridge holder does not rotate the bypass housing, but instead pushes the bypass housing distally to disengage the engagement recess from a locked position with the upper hub. Once the medicated module is transformed to triggering state, a step down edge is aligned with a portion of the distal or lower end of the upper hub that allows the bypass housing to move in a proximal direction when rotated by engagement with the needle guard when it is moved proximally. Ultimately, this rotation of the bypass housing results in the bypass housing being in a triggerable state and then upon action of the needle guard upon it, further rotating and axially moving to a triggered state as described below. When the user pushes the needle guard against an injection site, the guard moves proximally relative to the outer housing. A biasing element is placed between the inside surface of the guard and the distal side of the lower hub. Preferably, the biasing element is a compression spring that preferably is in a pre-compressed state. Movement of the guard further compresses the biasing element exerting a force in the proximal direction on the lower hub and the bypass housing urging them both to move proximally. Movement of the guard also triggers the bypass housing to rotate. Because the step down edge is in the triggering position, the bypass housing rotates and then moves axially in the proximal direction moving the reservoir along with the bypass housing and causing the needle cannula in the upper and lower hubs to become fluidically engaged with the medicament in the reservoir.

As the module mechanism does not require the user to access external features on the module for the purposes of actuation, the number of components and subsequent module size can be reduced/optimized. These factors make the mechanism ideal for a single-use, high-volume manufacture, and disposable device application. Alternatively, as the actuation is driven by a single action, the system lends itself to a resettable actuation mechanism. The preferred embodiment described below is the single use (non-resettable) version. The rotating bypass housing and lower hub in combination with a biasing force, preferably from a compression spring, causes theses parts to rotate and then to move axially as the needle guard is retracted. The needle guard is restrained rotationally with regard to the outer housing, but is free to move axially, between defined constraints, within the outer housing. In one embodiment a rib on the guard outer wall engages a channel on the inner surface of the outer housing to prevent the guard from rotating during linear movement relative to the outer housing.

Once attached to the cartridge holder, the user pressing the distal face of the needle guard against the skin causes axial motion of the needle guard in the proximal direction. This axial motion of the guard causes a rotation of the bypass housing, preferably through the engagement and action of an inward-facing drive tooth on the guard as it travels in a drive track having a non-linear path, which is located on the outer surface of the bypass housing. The lower hub, which preferably contains a double-ended needle cannula, also rotates and moves axially as the bypass housing rotates. It is this axial movement of the lower hub that results in the double ended needles located in the upper hub and the lower hub piercing the reservoir seals, moving it from a state of priming to combination dose delivery.

Further axial and proximal movement of the needle guard is required in order to pierce the skin, which compresses the biasing member creating a force that acts on the lower hub to result in the axial movement of the reservoir in the proximal direction. In normal use, once the drug has been dispensed and the needle is removed from the skin, the needle guard is allowed to return axially in the distal direction under the relaxation of the biasing member as it releases its stored energy. At some point along its return travel, a lock out mechanism is triggered locking out the needle guard from further use or exposing the needle. Should the user remove the device from the skin without dispensing fluid, but after the "commit" point has been passed, the needle guard would return to an extended position and lock out as previously described.

The medicated module assembly as described herein is attachable to a drug delivery device, preferably a pen shaped injection device, through an upper hub holding a first double-ended needle cannula and a connector configured for attachment to a drug delivery device. The hub can be a separate part from the housing or integral, for example molded as part of the housing. The connector can be any connector design, such as threads, snap fits, bayonet, luer lock, or combination of these designs.

Preferably, two needle cannula are used, a distal cannula and a proximal cannula, with both cannulae preferably being doubled-ended for piercing a septum or seal and for piercing skin. The distal needle is mounted in a lower hub and the proximal needle is mounted in the upper hub of the outer housing, each using any technique known to those skilled in the art, such as welding, gluing, friction fit, over-molding and the like. The medicated module assembly also contains a biasing member, preferably a compression spring. The biasing member is preferably in a pre-compressed state and positioned between the proximal inner face of the needle guard and the distal face of the lower hub. Although a preferred biasing member is a spring, any type of member that produces a biasing force will work.

The medicated module assembly of our invention automatically, once triggered, changes state from (1) a pre-use or priming state, where a small amount of primary medicament flows in a bypass around the reservoir containing a single dose of the secondary medicament, to (2) a ready-to-use or combination dose state, where both the upper and lower cannulae are in fluidic engagement with the fixed dose of the second medicament within the module and where a set dose of the primary medicament can be injected along with the non-settable single dose of secondary medicament in the reservoir, and finally to (3) a locked out state, where the needle guard is prevented from substantial proximal movement. The outer housing preferably has a window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both a pre-use priming position and a locked position of the guard after the medicated module assembly has been used to perform an injection.

Inside the bypass housing there is a cavity that contains the reservoir or capsule, which preferably comprises the single dose of medicament. As the needle guard is retracted during an injection, the reservoir is moved proximally with the bypass housing causing the seals of the reservoir to be pierced at its top and bottom by the needle cannula such that the medicament can be expelled from the reservoir during dose delivery. When connected to a drug delivery device containing a first medicament and prior to piercing the seals of the reservoir, the needle cannulae are only in fluid communication with the first medicament and a fluid flow path that bypasses the capsule. Preferably, a channel on the outside of the reservoir or alternatively on the inside surface of the bypass housing is part of this fluid flow path and is used in the priming function of the drug delivery device.

The medicated module of our invention may be attachable to a drug delivery device. The medicated module may comprise an outer housing having a proximal end, a distal end, and an inner surface. The proximal end may have an upper hub and a connector configured for attachment to a drug delivery device. A bypass housing may be located inside the outer housing. The bypass housing may be configured to move both rotationally and axially relative to the outer housing. The bypass housing may comprise an outer surface and a step down edge at a proximal end that may allow the bypass housing to move proximally. A reservoir may be located within the bypass housing comprising a medicament.

The medicated module may comprise a fluid flow path that bypasses the reservoir, i.e. a bypass. In one embodiment the bypass or flow path that bypasses the reservoir comprises a channel on the outside of the reservoir. In another embodiment the bypass or flow path that bypasses the reservoir comprises a channel on the bypass housing, e.g. on the inner surface of the bypass housing.

The medicated module may further comprise a needle guard having inner and outer walls, where the inner wall engages the bypass housing to cause movement of the bypass housing. For example, an inward-facing drive tooth on the needle guard may engage a drive track, which is located on the outer surface of the bypass housing and be configured to cause rotation and/or axial movement of the bypass housing. The drive track may have a non-linear path. The needle guard outer wall may be slidably engaged with the inner surface of the outer housing to prevent the needle guard from rotating during linear movement relative to the outer housing.

A biasing member may be engaged between the needle guard and a lower hub located at the distal end of the bypass housing to bias the needle guard into an extended or guarded position. The lower hub may comprise a double ended needle cannula, e.g. an injection needle. In the guarded position, the needle guard may cover the double ended needle cannula of the lower hub, e.g. to prevent accidental needle sticks.

The engagement and configuration of the reservoir inside the bypass housing with the lower hub is selected to allow the lower hub to move a greater proximal distance than the reservoir so as to allow the proximal end of needle to come into fluid communication with the medicament in the reservoir. The lower hub may comprise protrusions, legs, or steps configured to mechanically cooperate with corresponding features on the bypass housing, such as indents, stand-off pockets, ribs, steps, or the like. In one embodiment, the lower hub may comprise legs configured to mechanically cooperate with stand-off pockets on the bypass housing. Rotation of the bypass housing may bring a lower stand-offs in alignment with legs and the lower hub may be free to move axially in proximal direction relative to the bypass housing. Other examples may comprise corresponding features, as e.g. named previously. The axial movement of the lower hub relative to the bypass housing may allow the proximal end of needle to come into fluid communication with the medicament in the reservoir.

The medicated module according to the invention may comprise a locked state and an unlocked state. The upper hub may have a cutout that allows functional access to a portion of the proximal end of the bypass housing to allow the medicated module to change state from locked to unlocked. In the locked state the bypass housing is in a first position. In the unlocked state the bypass housing is in a second position. The bypass housing may be configured to be moved axially in a distal direction from the first position to the second position. The bypass housing may be configured to be rotated from the first position to the second position.

When in the locked state the needle guard cannot rotate the bypass housing. When in the unlocked state, axial motion or movement of the needle guard in proximal direction may cause the bypass housing to rotate, e.g. through a guiding engagement between the needle guard and the bypass housing.

In the locked state, the needle guard may be axially locked to the bypass housing, e.g. by a needle guard protrusion being blocked against a feature of the bypass housing. In the unlocked state, the bypass housing is rotated from a first position to a second position, e.g. to a position where the protrusion of the needle guard is not blocked. In the unlocked state retraction of the needle guard causes the bypass housing to rotate. In one embodiment the feature of the bypass housing may comprise a drive track having a straight portion configured to block the needle guard and a helical portion configured to cause rotation and/or axial movement of the bypass housing upon axial movement of the needle guard.

In the locked state, the bypass housing may be rotationally locked to the upper hub, e.g. by an engagement recess being locked to an upper hub tab. As the bypass housing cannot rotate, the needle guard cannot move axially in proximal direction due to the engagement with the bypass housing. In the unlocked state, the bypass housing is moved axially in distal direction from the first position to the second position, e.g. to a second position where the recess in unlocked from the upper hub tab. In the unlocked state retraction of the needle guard causes the bypass housing to rotate.

The biasing member may be engaged between the needle guard and the lower hub. In the unlocked state, retraction or axial movement of the needle guard in proximal direction may cause the bypass housing to be rotated. Retraction or axial movement of the needle guard in proximal direction may further compress the biasing member exerting a force on the lower hub and the bypass housing urging them both to move proximally. Proximal movement of the lower hub may cause the needle cannula of the lower hub to become fluidly engaged with the medicament in the reservoir.

The medicated module may be in the locked state when not attached to a drug delivery device.

The medicated module may be in the unlocked state when attached to a drug delivery device.

In the unlocked state, proximal movement of the bypass housing may cause the medicament in the reservoir to become engaged with an upper or proximal needle cannula. The upper or proximal needle cannula may be located in the upper hub of the medicated module. The upper needle cannula may be located at a distal end of a drug delivery device attached to the medicated module. In either case, the upper cannula, when fluidly engaged with the medicament in the reservoir, may fluidly engage with a medicament in a reservoir of the drug delivery device. This would allow the two medicaments from the two separate reservoirs to be dispensed through one dispense interface, e.g. the distal needle cannula or injection needle of the medicated module according to the invention.

Another aspect of the invention relates to a drug delivery device attachable to a medicated module according to the invention. The drug delivery device may comprise a reservoir or primary reservoir of medicament containing at least one drug agent and a dose button operably connected to the primary reservoir of medicament. The drug delivery device may further comprise features configured to interact or functionally access to a portion of the proximal end of the bypass housing allowing the medicated module to change state from locked to unlocked. When the drug delivery device is attached to the medicated module, the medicated module in is the unlocked state.

The features configured to interact or functionally access to a portion of the proximal end of the bypass housing may be configured to cause the bypass housing to be moved from the first position to the second position. The features could be axially or radially projecting tabs. In one embodiment rotation tabs may be arranged to cause the bypass housing to be rotated from a first position to a second position, when the medicated module is attached to the drug delivery device. In another embodiment the tabs may be arranged to cause the bypass housing to be moved axially from a first position to a second position, e.g. in distal direction, when the medicated module is attached to the drug delivery device.

Another aspect of the invention relates to a drug delivery system comprising a single dose setter and a single dispense interface configured to dispense two medicaments from two reservoirs through the single dispense interface. In one embodiment, the single dispense interface may be an injection needle. The drug delivery system may comprise a flow path that bypasses one reservoir. The bypass flow path may be used for priming, e.g. removing air from the injection needle prior to injection. The drug delivery system may comprise a medicated module according to the invention and a drug delivery device according to the invention.

A further aspect of the invention relates to a method of dispensing a fixed dose of one medicament and a variable dose of a primary medicament from separate reservoirs that involves the steps of first attaching a medicated module to a delivery device set in a pre-use or prime only state. Attaching to the primary device rotates or moves the bypass housing from the first locked state to a triggerable state. When in the locked state the needle guard cannot rotate the bypass housing to engage the two needle cannula into the reservoir because either the straight portion of the non-linear track blocks the needle guard protrusion or the engagement recess is locked to the upper hub tab. The user can prime the dose delivery device using only the primary medicament and bypassing the second medicament. After priming the user begins the injection and the needle guard begins to retract and the module automatically changes to second state that allows a combination delivery of the two medicaments. Upon completion of the delivery procedure and retraction of the needle from the injection site, the extension of the needle guard automatically changes the module to a third state.

During dispense, substantially the entire amount of second medicament has been expelled as well as the selected or dialed dose of the first medicament, through the single dispense interface. The reservoir preferably contains a flow distributor to ensure that substantially all the single dose of secondary medicament is forced out of the capsule by the primary medicament during an injection. The flow distributor can be a separate stand-alone insert or pin. Alternatively the flow distributor and the capsule together can be manufactured or assembled as a one-piece component where the flow distributor is integral with the reservoir or capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g., glass, plastics or specific polymers, for example, TPE (thermo plastic elastomer); LSR (liquid silicone rubber); LDPE (low density polyethylene); and/or any kind of medical grade rubber, natural or synthetic.

By "substantially all" we mean that at least about 80% of the second medicament is expelled from the drug delivery device, preferably at least about 90% is expelled. In the third state, preferably the module is locked so as to prevent a second delivery or insertion by means of a locking mechanism.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module of our invention can be designed for use with any drug delivery device with an appropriate compatible interface. However, it may be preferable to design the module in such a way as to limit its use to one exclusive primary drug delivery device (or family of devices) through employment of dedicated/coded/exclusive features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary drug delivery device is used more than once and therefore is multi-use; however, the drug delivery device may also be a single use disposable device. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the patient attempt to reuse a previously used medicated module, our invention includes the locking needle guard that is activated after a first predefined travel/retraction of the guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature of our invention is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Our invention also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIGS. 11a, 11b, 11c are transparent views of one embodiment of the proximal portion of the medicated module of our invention as it connects with the cartridge holder of FIG. 7 and interacts with the bypass housing of FIG. 10;

DETAILED DESCRIPTION

Figure 1:
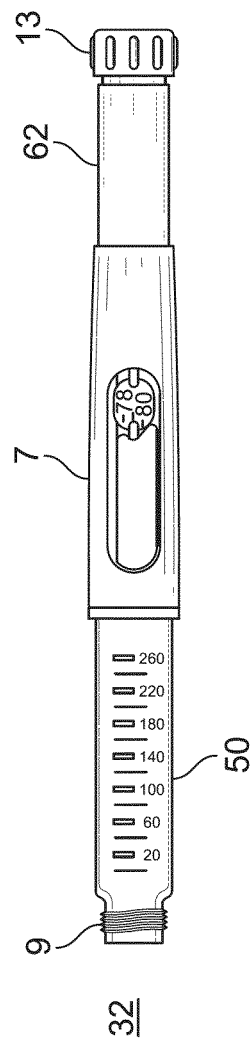
FIG. 1 illustrates one possible drug delivery device that can be used with the present invention.
Figure 5A:
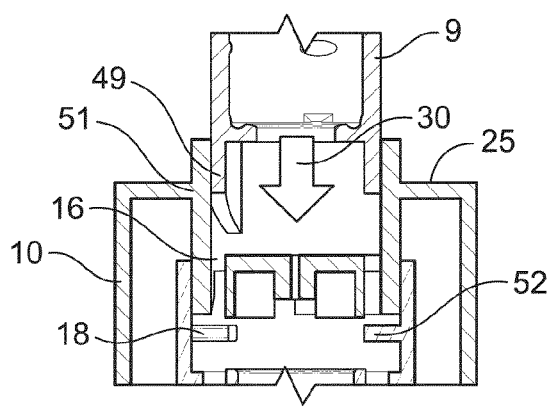
FIGS. 5a, 5b are sectional views of one embodiment of the proximal portion of the medicated module of our invention as it connects with a cartridge holder of a drug delivery device.
Figure 5B:
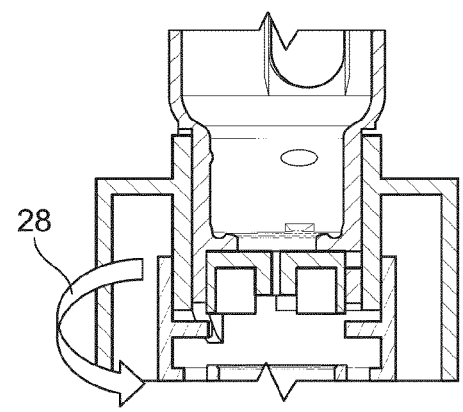

The present invention administers a fixed predetermined dose of a secondary drug compound (medicament) and a variable dose of a primary or first drug compound through a single output or drug dispense interface. Setting the dose of the primary medicament by the user automatically determines the fixed dose of the second medicament, which preferably is a single dose contained in a capsule or reservoir having an integral flow distributor. In a preferred embodiment the drug dispense interface is a needle cannula (hollow needle). FIG. 1 illustrates one example of a drug delivery device 7 that the medicated module 4 (see FIG. 2 or 5) of our invention can be attached to the connection means 9 on cartridge holder 50 of distal end 32. Each medicated module is preferably self-contained and provided as a sealed and sterile disposable module that has an attachment means 8 compatible to the attachment means 9 at the distal end 32 of device 7. Although not shown, the medicated module could be supplied by a manufacturer in a protective and sterile container, where the user would peel or rip open a seal or the container itself to gain access to the sterile medicated module. In some instances it might be desirable to provide two or more seals for each end of the medicated module.

Figure 2:
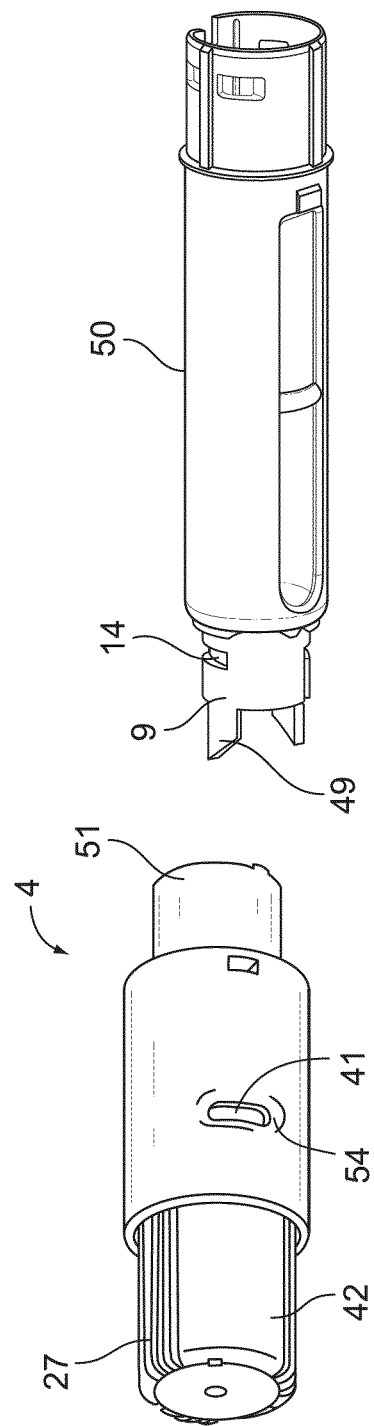
FIG. 2 illustrates an embodiment of the medicated module of the present invention, where the medicated module is separated from an attachable cartridge holder of the drug delivery device of FIG. 1.

Any known attachment means 8 can be used to attach the medicated module to the chosen drug delivery device, including all types of permanent and removable connection means, such as threads, snap locks, snap fits, luer locks, bayonet, snap rings, keyed slots, and combinations of such connections. FIG. 1 illustrates the attachment means 9 as threaded connection and FIG. 2 shows an alternate unique connection that is keyed specifically to a corresponding connection on medicated module 4, respectively. More specifically, the attachment means includes an axially extending cartridge holder tab 49 that, as explained in detail below, engages the proximal end of the bypass housing 52, preferably rotation tabs 15 through cutout 16 of upper hub 51.

Figure 3A:
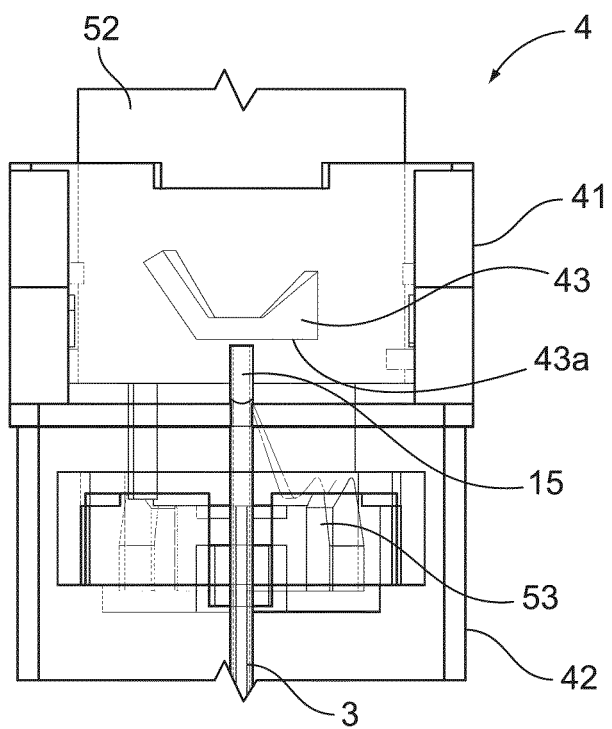
FIGS. 3a, 3b illustrate transparent views of one embodiment of the bypass housing having a non-linear track on the outer surface.
Figure 3B:
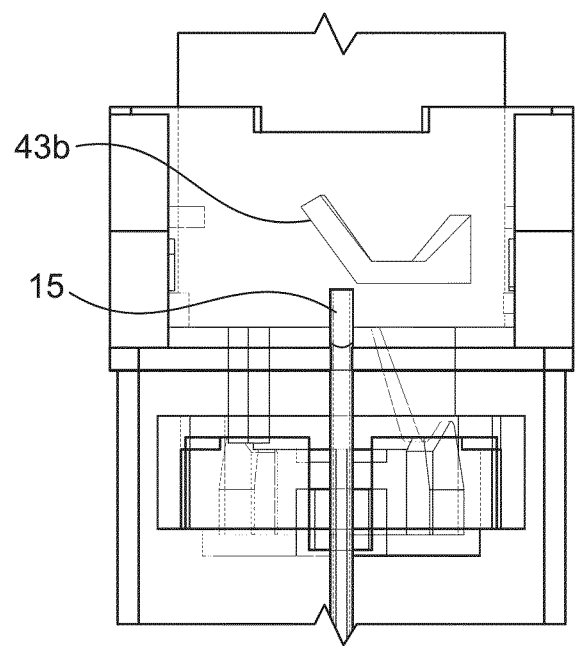

FIGS. 3a and 3b show one embodiment where needle guard 42 has a radial protrusion on the inside surface that engages a non-liner track on the outside surface of bypass housing 52. This track has a straight portion 43a and a helical portion 43b. As illustrated in FIG. 3a, when the medicated module 4 is in the locked state, the radial protrusion 15 is blocked from axial movement in the proximal direction by the flat portion 43a of track 43. This prevents the guard 42 from moving proximally. The module 4 is transformed to the triggering state when a cartridge holder 50 is attached to upper hub 51. As explained in detail below, attaching the cartridge holder causes the bypass housing 52 to rotate. This position is illustrated in FIG. 3b. In this triggering state, movement of the guard in the proximal direction will cause radial protrusion 15 to engage the helical portion 43b of track 43. As the guard retracts, protrusion 15 will ride along the helical portion and cause the bypass housing to further rotate. This will then fire (i.e., connect the reservoir 22 to needles 3 and 5) the module as the bypass housing also moves proximally along with the lower hub 53 therefore engaging the primary pack.

Firing of the module 4 is assisted by spring 48 (see FIG. 6) and results in the upper and lower needle cannula, 5 and 3, piercing reservoir 22. The embodiment shown in FIG. 6 has the benefit of the second medicament as a single dose being contained entirely within reservoir 22, hence minimizing the risk of material incompatibility between the second medicament and the materials used in the construction of the medicated module 4, specifically housing 10, bypass housing 52, or any of the other parts used in the construction of the medicated module.

Figure 12:
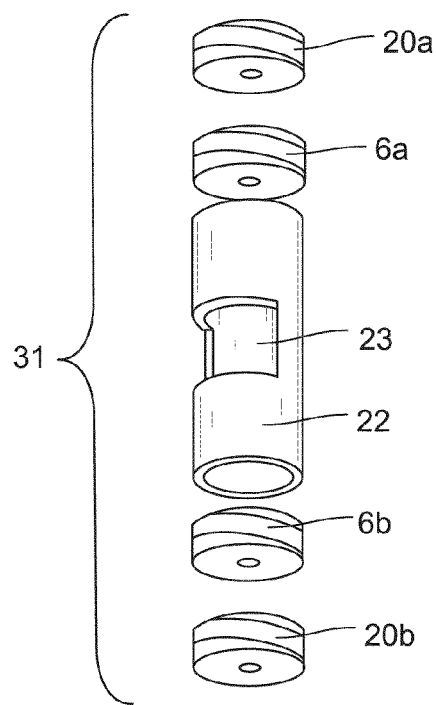
FIG. 12 is an exploded view of the capsule or reservoir containing the second medicament.
Figures 13, 14:
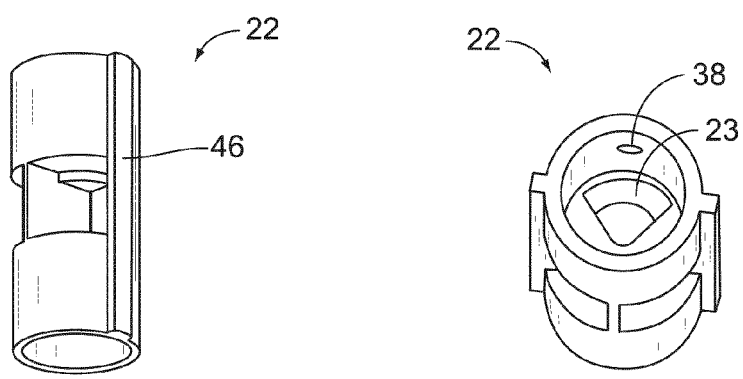
FIG. 13 is a perspective view of the reservoir showing part of the bypass.
FIG. 14 is another perspective view of the reservoir showing the flow distributor.

To minimize the residual volume of the second medicament, caused by recirculation and/or stagnant zones, that might remain in capsule 31 at the end of the dispense operation, it is preferable to have a flow distributor 23 as an integral part of reservoir 22 (see FIGS. 12,13 and 14). The reservoir 22 containing the single dose of the secondary medicament can be sealed with septa 6a and 6b, which are fixed to the capsule using keepers or plugs 20a and 20b. Preferably the keepers have fluid channels that are in fluid communication with needles 3 and 5 and with bypass 46, which is preferably part of the inside surface of bypass housing 52. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 should ensure that at least about 80% of the second medicament is expelled from reservoir 22 through the distal end of needle 3. Most preferably at least about 90% should be expelled. Ideally, displacement of the first medicament in a primary reservoir (not shown) contained in cartridge holder 50 and through the capsule 31 will displace the single dose of the second medicament stored in reservoir 22 without substantial mixing of the two medicaments.

Figure 4:
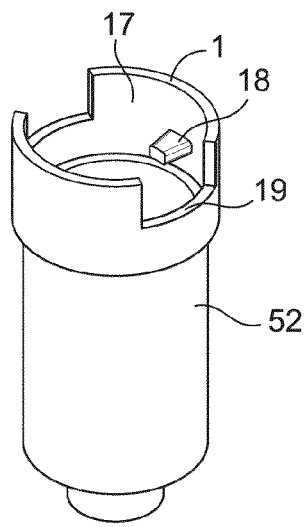
FIG. 4 illustrates a perspective view of one embodiment of the bypass housing having a rotation tab on the inside surface.

Prior to the attachment of medicated module 4 to cartridge holder 50 of the drug delivery device 7, the medicated module is in the first locked position such that the bypass housing 52 cannot move proximally to engage needle cannulae 3 and 5. As explained previously, the non-linear track 43 prevents the needle guard from moving proximally and from rotating the bypass housing. The proximal portion 1 or radial tab 18 of the bypass housing 52 (see FIG. 4) is in contact the distal end of the upper hub 51, which also prevents the bypass housing from moving proximally until it reaches a defined rotational position.

Attachment of the medicated module 4 to the cartridge holder 50 (see FIG. 2) with tabs 49 in direction 30 (see FIG. 5a) causes the tabs 49 to protrude through cutouts 16. As the cartridge holder is further attached through rotating motion 28 (see FIG. 5b), tabs 49 engage rotation tabs 18 that project radially from the inside surface 17 of the bypass housing. This engagement causes the bypass housing to rotate with the cartridge holder bringing the module to the triggering state described above where the radial protrusion 15 can be engaged with the helical portion 43b of track 43. Once in the triggering state, there is nothing else to prevent the bypass housing from rotating and moving proximally as a result of proximal movement (i.e., retraction) of needle guard 42.

An alternate bypass housing and upper hub design is shown in FIGS. 7, 8 and 9a-9c. In this design the cartridge holder 50 has tabs 49 shaped as radial lugs that extend through the cutout 16 in the upper hub 51 and engage axially with extending rotation tabs 18. As illustrated in the sequence shown in FIGS. 9a-9c, as cartridge holder 50 is inserted and rotated during connection to the upper hub, rotation of lugs 49 cause rotation of tabs 18 and of the bypass housing a sufficient distance such that protrusion 15 will engage the helical portion 43b of track 43 (see FIGS. 3a and 3b). The medicated module is thus placed in the triggering state.

Figure 10:
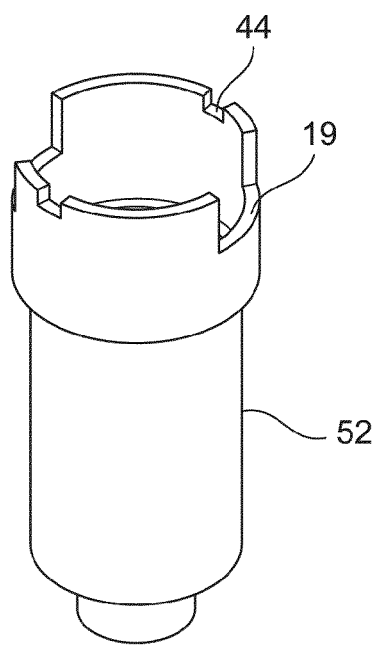
FIG. 10 illustrates a perspective view of another embodiment of the bypass housing having an engagement recess on the proximal end.
Figure 11C:
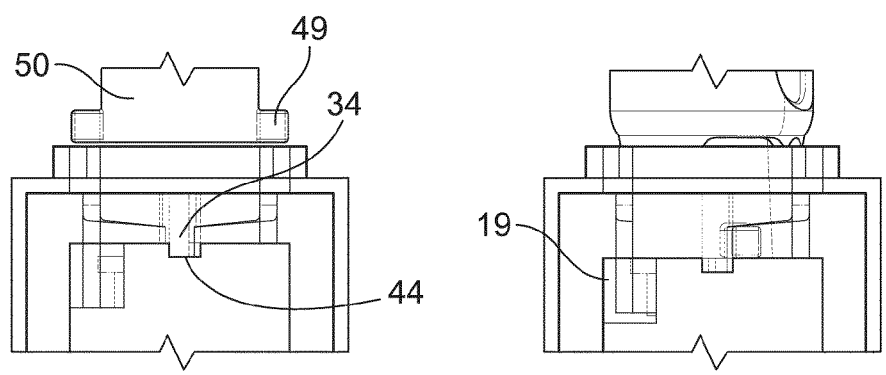

Yet another possible design of the bypass housing and upper hub is illustrated in FIG. 10, where the bypass housing does not have the rotation tabs and instead uses one or more engagement recesses 44 that lock into upper hub tabs 34. Tab 34 engages recess 44 to prevent the bypass housing from rotating and moving proximally when the medicated module is in the locked state. This eliminates the need for the straight portion 43a of track 43. However, the helical portion 43b is still required to rotate the bypass housing when the module has been set to the triggering state. As illustrated in FIGS. 11a-11c, attachment of cartridge holder 50 causes the bypass housing to be pushed in the distal direction a sufficient distance so that the tab 34 disengages from recess 44. The bypass housing is now able to rotate and the module is in the triggering state.

For each of the above described possible embodiments, the medicated module is triggered or fired when the needle guard is retracted (moved proximally) during an injection or application of the guard to an injection site. As the guard moves proximally the protrusion on the guard engages the track on the outside surface of the bypass housing causing the bypass housing to rotate because the guard is constrained from rotation by its engagement with the outer housing. Rotation of the bypass housing moves the step down edge 19 into alignment with the distal side of the upper hub such that the force exerted by the biasing element 48, lower hub 53 and needle guard 42 causes the bypass housing to move axially in the proximal direction. This axial movement causes the two needle cannulae 3 and 5 to engage reservoir 22.

The attachment of the cartridge holder 50 to the medicated module 4 also causes needle 5 to penetrate a septum (not shown) sealing the distal end of the cartridge of primary medicament (not shown) positioned in cartridge holder 50 of the multi-use device 7. Once needle 5 has passed through the septum of the cartridge, fluid connection is made between the first medicament and the needle 5. At this point, the system can be primed by dialing out a small number of units (or cocking the device if only a single dose selection is possible) using dose dial sleeve 62. Once the device 7 is primed, activation of the needle guard 42 allows dispense of the medicaments by subcutaneously injecting the medicaments via activation of a dose button 13 on device 7. The dose button of our invention can be any triggering mechanism that causes the dose of the first medicament that was set by the dose dial sleeve 62 to move towards the distal end 32 of the device. In a preferred embodiment the dose button is operably connected to a spindle that engages a piston in the primary reservoir of the first medicament. In a further embodiment the spindle is a rotatable piston rod comprising two distinct threads.

Figure 6:
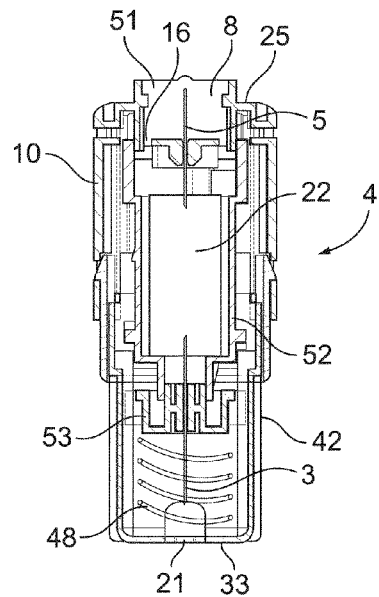
FIG. 6 illustrates a sectional perspective view of one embodiment of the medicated module of our invention.
Figure 7:
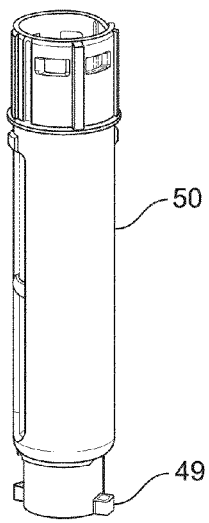
FIG. 7 illustrates a perspective view of one type of cartridge holder that can be attached to the medicated module of FIG. 6.
Figure 8:
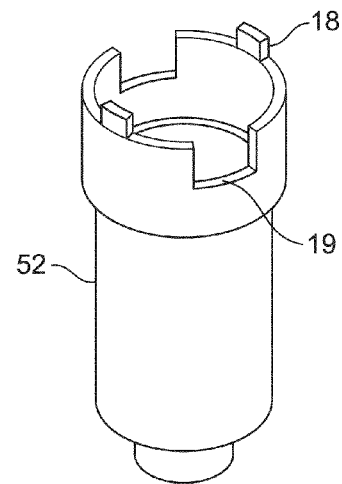
FIG. 8 illustrates a perspective view of another embodiment of the bypass housing having rotation tabs projecting axially from the proximal end.
Figure 9A:
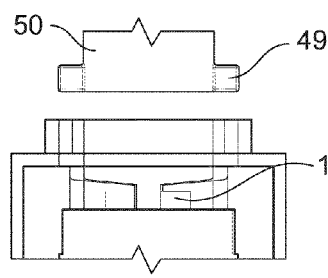
FIGS. 9a, 9b, 9c are transparent views of one embodiment of the proximal portion of the medicated module of our invention as it connects with the cartridge holder of FIG. 7 and interacts with the bypass housing of FIG. 8.
Figure 9B:
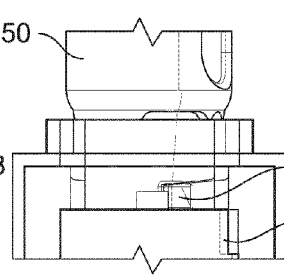
Figure 9C:
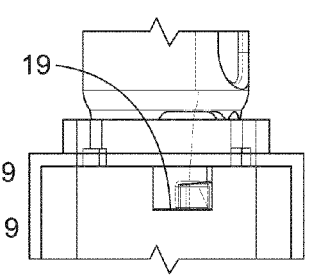

One embodiment of the medicated module 4 of our invention is illustrated in FIG. 6. In this embodiment the medicated module 4 contains a capsule 31 comprising a reservoir 22, two keepers 20a and 20b, and two seals 6a and 6b. Reservoir 22 contains a fixed single dose of a secondary medicament. In some cases this secondary medicament may be a mixture of two or more drug agents that can be the same or different from the primary drug compound in the drug delivery device 7. Preferably the capsule is permanently fixed within the medicated module, however, in some cases it may be preferred to design the module such that the capsule can be removed when empty and replaced with a new capsule.

In the embodiments shown in FIG. 12, capsule 31 has ends that are sealed with pierceable membranes or septa 6a and 6b that provide a hermetically sealed and sterile reservoir 22 for the second medicament. A primary or proximal engagement needle 5 can be fixed in hub 51 connected to the proximal end of housing 10 of the module and configured to engage capsule 31 at some predetermined axial travel of the needle guard moving in the proximal direction during injection. The outlet, or distal needle 3, is preferably mounted in lower hub 53 and initially protrudes into lower keeper 20b. The proximal end of needle 3 pierces the lower septum 6b as the lower hub is pushed by biasing member 48 in the proximal direction as the needle guard 42 is refracted a predetermined distance into outer housing 10 during injection.

As mentioned, before attachment to the drug delivery device the module is in a locked state. This can be determined from window 54 that contains indicia illustrating the locked state. When attached to the delivery device, the bypass housing is moved to a triggering state and this can also potentially be shown in window 54. And finally, after the module has been triggered (or fired) during use, a third indicia can be viewed through window 54. Preferably, the indicia appear on an indicator 41 that shows through window 54 to inform the user of these three possible states of the medicated module. The indicator is preferably a color stripe or band on the outer surface of one of the various parts of the medicated module visible through an aperture 54 in the outer body. One color could designate the locked state, another color the triggering state or prime state of the module and a third color would indicate that the module is in finished or locked state. Additionally, another color could be used to denote the transition through the trigger or "commit" point in case a user stops injection after trigger point but before "commit" point. For example, a yellow color could indicate the locked state, a green color could indicate the triggering state and a band of red color could be used to indicate that the module has been used and is locked. An orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that the needle guard is made form a transparent material.

The needle guard 42 is slidably engaged with the inner surface of outer housing 10, preferably by engagement of one or more ribs 27 on the outer surface with channels (not shown) on the inside surface the outer housing. Of course, the rib and channel can be reversed where the channels are located on the outside surface of needle guard 42. Preferably, retention snaps (not shown) prevent the guard from disengaging the outer housing at its fully extended position. A portion of the proximal end of housing 10 defines an upper hub 51 that holds needle 5. Optionally, as illustrated in FIG. 5, a shoulder cap 25 may be added to the proximal outer surface of outer housing 10. This shoulder cap can be configured to serve as indicia to identify to a user the type/strength of medicament contained in the module. The indicia can be tactile, textual, color, taste or smell.

The compression spring 48 is positioned between the distal end of lower hub 53 and the inner proximal face of guard 42 to bias the guard 42 into an extended (guarded) position as illustrated in FIG. 6. Upon assembly, the proximal end of spring 48 positioned against lower hub 53, which is prevented from moving axially in the proximal direction by engagement of the proximal edge of the bypass housing with the distal side of the upper hub. As the needle guard 42 is pushed against an injection site it retracts proximally up into the outer housing 10, but is constrained from rotating by engagement of the ribs and channels. Preferably, the axial movement of the needle guard in the proximal direction causes the lower hub and bypass housing to also move proximally as the bypass housing is no longer prevented from rotating. The engagement and configuration of the reservoir 22 with the lower hub 53 is selected to allow the lower hub to move a greater proximal distance than the reservoir so as to allow the proximal end of needle 3 to come into fluid communication with the second medicament.

One possible feature of our medicated module assembly is the inclusion of user feedback that is given when the assembly is used. In particular, the assembly could emit an audible and/or tactile "click" to indicate to the user that they have firstly triggered the device and potentially secondly reached a "commit" point such that the needle guard will lock safely out upon completion of the injection/removal of the guard from the injection site.

As mentioned, the distal end of the guard 42 has a planar surface 33 that provides an added measure of safety and reduces the pressure exerted by the guard on the injection site during an injection with our needle assembly. Because the planar surface 33 substantially covers access to needle 3 a user is prevented from gaining access to the distal tip of the needle after the assembly is in the locked position. Preferably, the diameter of needle pass through hole 21 in the planar surface is no more than 10 times that of the outer diameter of needle cannula 3.

In any of the above described embodiments of our invention the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

Figure 11C:
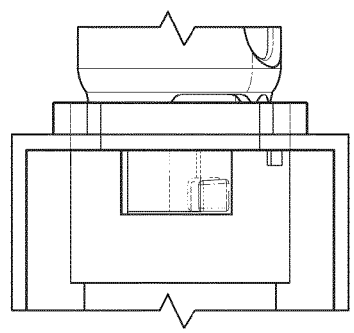

To minimize diffusion of the secondary medicament contained in the capsule within the medicated module into the primary medicament during dispense of the medicaments the reservoir 22 has an integral flow distributor 23. This flow distributor also ensures efficient expulsion of the second medicament from the system and greatly minimizes residual volume. One possible embodiment of the reservoir 22 and flow distributor 23 is illustrated in FIGS. 9-11. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable, for example a material like COP. The flow distributor 23 is configured and positioned in reservoir 22 such that the secondary medicament fills flow channels that are defined by the shape and location of one or more channels (not shown) inside the reservoir. The shape of the flow channels can be optimized for a plug flow of medicament by varying the dimensions of the flow distributor and/or channels. The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, comprising,
a locked state and an unlocked state;
an outer housing having a proximal end, a distal end, and an inner surface, where the proximal end has an upper hub and a connector configured for attachment to a drug delivery device;
a bypass housing comprising an outer surface and a step down edge at a proximal end, wherein the bypass housing is located inside the outer housing and is configured to move both rotationally and axially relative thereto;
a reservoir within the bypass housing comprising a medicament;
a needle guard having inner and outer walls, wherein the inner wall is configured to engage the bypass housing to cause movement of the bypass housing, and wherein the needle guard outer wall is slidably engaged with the inner surface of the outer housing to prevent the needle guard from rotating during linear movement relative to the outer housing; and
a biasing member engaged between the needle guard and a lower hub located at the distal end of the bypass housing, configured to bias the needle guard into an extended or guarded position;
wherein the upper hub has a cutout in a proximal end face of the upper hub that allows functional access to a portion of the proximal end of the bypass housing to allow the medicated module to change state from the locked state to the unlocked state, wherein in the locked state the needle guard cannot rotate the bypass housing such that the distal needle cannula is not fluidly engaged with the secondary medicament in the secondary reservoir, and wherein in the unlocked state axial movement of the needle guard in a proximal direction causes the bypass housing to rotate and the biasing member to be compressed exerting a force on the lower hub and the bypass housing urging them both to move proximally, wherein when the lower hub is moved proximally the distal needle cannula of the lower hub is caused to become fluidly engaged with the secondary medicament in the secondary reservoir.

2. The medicated module of claim 1, wherein in the locked state the needle guard is axially locked to the bypass housing.

3. The medicated module of claim 1, wherein in the locked state the bypass housing is in a first position and wherein in the unlocked state the bypass housing is in a second position.

4. The medicated module of claim 3, wherein the bypass housing is configured to be rotated from the first position to the second position.

5. The medicated module of claim 3, wherein the bypass housing is configured to be moved axially in a distal direction from the first position to the second position.

6. The medicated module of claim 1, wherein the inner wall of the needle guard has a radial protrusion and the outer surface of the bypass housing has a nonlinear track configured to engage the radial protrusion to cause rotation and/or axial movement of the bypass housing upon axial movement of the needle guard.

7. The medicated module of claim 6, wherein the nonlinear track comprises a straight or flat portion and a helical portion, wherein in the locked state the flat portion is engaged with the needle guard protrusion, and in the unlocked state, the helical portion is engaged with the needle guard protrusion.

8. The medicated module of claim 7, wherein the bypass housing has a rotation tab projecting radially from an inner surface.

9. The medicated module of claim 7, wherein the bypass housing has a rotation tab projecting axially from the proximal end.

10. The medicated module of claim 6, wherein the bypass housing has an engagement recess in the proximal end.

11. The medicated module of claim 10 wherein the engagement recess is configured to engage a tab projecting distally from the upper hub to prevent axial movement and rotation of the bypass housing.

12. The medicated module of claim 1 wherein the lower hub holds a double-ended needle cannula, wherein when the needle guard is in the guarded position the double ended needle cannula of the lower hub is covered by the needle guard.

13. The medicated module of claim 1, wherein the upper hub further comprises a proximal needle cannula, wherein in the unlocked state, when the bypass housing is moved proximally, the medicament in the reservoir is caused to become engaged with the proximal needle cannula.

14. The medicated module of claim 1, wherein the reservoir is a single molded component having an internal cavity with an integral flow distributor.

15. The medicated module of claim 1 further comprising a fluid flow path that bypasses the reservoir.

16. The medicated module of claim 15, wherein the fluid flow path that bypasses the reservoir comprises a channel on the outside of the reservoir.

17. The medicated module of claim 15, wherein the fluid flow path that bypasses the reservoir comprises a channel on the bypass housing, e.g. on the inner surface of the bypass housing.

18. The medicated module of claim 1 wherein the medicament comprises a liquid medicament.

19. The medicated module of claim 1 wherein the medicament comprises one of a GLP-1 or a premix of insulin and a GLP-1.

20. The medicated module of claim 1, wherein prior to attachment to a drug delivery device the medicated module is in the locked state such that it is not possible to inject the contents, and wherein after attachment to a drug delivery device, the medicated module is in an unlocked state such that medicament from the attached drug delivery device can be dispensed and upon retraction of the guard a combined dose of medicaments from the drug delivery device and the reservoir can be dispensed.

21. The medicated module of claim 1, wherein in the locked state the bypass housing is rotationally locked to the upper hub.

22. A drug delivery device attachable to a medicated module according to claim 1, wherein the drug delivery device comprises a reservoir of medicament containing at least one drug agent and a dose button operably connected to the reservoir, and further comprises axially or radially projecting tabs configured to functionally access a portion of the proximal end of the bypass housing allowing the medicated module to change state from locked to unlocked.

23. A drug delivery device according to claim 22, wherein the tabs are configured to cause the bypass housing to be moved from the first position to the second position.

24. A drug delivery device according to claim 22, wherein the tabs are arranged to cause the bypass housing to be rotated from the first position to the second position, when the medicated module is attached to the drug delivery device.

25. A drug delivery device according to claim 22, wherein the tabs are arranged to cause the bypass housing to be moved axially from the first position to the second position in distal direction, when the medicated module is attached to the drug delivery device.

26. A drug delivery system to deliver two or more medicaments operable through a single dispense interface, comprising, a primary reservoir of medicament containing at least one drug agent;

a dose button operably connected to the primary reservoir of medicament;

a single dispense interface configured for fluid communication with the primary reservoir; and the medicated module of claim 1.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15
```

-continued

```
Ile Phe Leu Arg Val Ala Glu Glu Glu Met Gln Lys Ser Leu Asp Ser
            20                  25                  30
Thr Phe Thr Gly Glu Gly His
        35
```